US006186999B1

United States Patent
Chen

(10) Patent No.: US 6,186,999 B1
(45) Date of Patent: Feb. 13, 2001

(54) RIGID CLAMPABLE CANNULA

(75) Inventor: Ji-Feng Chen, Lakewood, OH (US)

(73) Assignee: The Cleveland Clinic Foundation, Cleveland, OH (US)

(*) Notice: Under 35 U.S.C. 154(b), the term of this patent shall be extended for 0 days.

(21) Appl. No.: 09/141,225

(22) Filed: Aug. 27, 1998

(51) Int. Cl.[7] .................................................. A61M 25/00
(52) U.S. Cl. ............................ 604/524; 604/523; 604/264
(58) Field of Search ............................ 604/96, 523, 524, 604/525, 530, 532, 96.01, 103, 264, 246, 249, 236; 138/155; 285/145.1, 144.1, 148.13, 223, 235, 238–241

(56) References Cited

U.S. PATENT DOCUMENTS

| | | | |
|---|---|---|---|
| 4,003,382 | * 1/1977 | Dyke | 128/349 |
| 4,133,303 | * 1/1979 | Patel. | |
| 4,357,860 | * 11/1982 | Krzak | 98/33 R |
| 4,564,014 | * 1/1986 | Fogarty et al. | 128/344 |
| 5,242,418 | * 9/1993 | Weinstein | 604/192 |
| 5,334,153 | * 8/1994 | McIntyre et al. | 604/99 |
| 5,360,401 | * 11/1994 | Turnland | 604/96 |
| 5,391,172 | * 2/1995 | Williams et al. | 606/108 |
| 5,425,714 | * 6/1995 | Johnson et al. | 604/102 |
| 5,445,646 | * 8/1995 | Euteneuer et al. | 604/96 |
| 5,458,615 | * 10/1995 | Klemm et al. | 604/96 |
| 5,571,135 | * 11/1996 | Fraser et al. | 604/96 |
| 5,578,009 | * 11/1996 | Kraus et al. | 604/96 |
| 5,591,138 | * 1/1997 | Vaillancourt | 604/263 |
| 5,653,684 | * 8/1997 | Laptewicz et al. | 604/22 |
| 5,674,192 | * 10/1997 | Sahatjian et al. | 604/96 |
| 5,695,469 | * 12/1997 | Segal | 604/104 |
| 5,755,108 | * 5/1998 | Segal | 604/109 |
| 5,882,334 | * 3/1999 | Sepetka et al. | 604/96 |
| 5,893,396 | * 4/1999 | Vagle | 138/120 |
| 6,062,267 | * 5/2000 | Fleming | 138/114 |

* cited by examiner

Primary Examiner—Richard K. Seidel
Assistant Examiner—Cris Rodriguez
(74) Attorney, Agent, or Firm—Calfee, Halter & Griswold LLP

(57) ABSTRACT

A clampable conduit comprising a generally rigid layer having a first end and a generally flexible tube generally coaxial with the rigid layer. The flexible tube extends axially in a first direction beyond the first end. The conduit also has a generally rigid sleeve moveable between a cover position, wherein the sleeve covers a first part of the flexible tube, and an uncovered position, wherein the sleeve does not cover the first part of a flexible tube to enable clamping of the conduit.

25 Claims, 3 Drawing Sheets

RIGID CLAMPABLE CANNULA

BACKGROUND OF THE INVENTION

The present invention is directed to a blood flow cannula, and more particularly, to a generally rigid clampable blood flow cannula.

Cannulas are often used to guide blood flow out of a person's heart and into a ventricle assist device which aids the heart in delivering blood to the body. A first end of the cannula is passed directly through the heart wall, and is fixed in place by sewing a fabric cuff to the outer wall of the heart. A second end of the cannula is then coupled to a conduit which delivers the blood to the ventricle assist device. It is known to manufacture cannulas of clear polymer tubing. However, such cannulas are susceptible to kinking, or may be squeezed shut by internal organs abutting against the cannula, which blocks the flow of blood.

In response to this problem, cannulas were developed which had a coiled wire disposed inside the cannula. The coiled wire provides support to avoid kinking and collapsing of the cannula. However, it is often necessary to clamp the cannula to temporarily block the flow of blood therethrough. Cannulas having a coiled wire may be difficult to clamp, and/or may not have sufficient resiliency to return to their original unclamped shape once the clamp is removed. Accordingly, there exists a need for a cannula which avoids kinking and inadvertent closure, but can be clamped and return to its original position when the clamp is removed.

SUMMARY OF THE INVENTION

The present invention is a generally rigid cannula which includes a clampable portion that can be clamped when it is desired to block the flow of blood therethrough. Upon removal of the clamp the clampable portion returns to its original shape, thereby allowing the flow of blood to resume through the cannula. The present invention also avoids inadvertent kinking.

More particularly, the present invention is a clampable conduit comprising a generally rigid section having a first end and a generally flexible section generally coaxial with the rigid section. The flexible section extends axially in a first direction beyond the first end. The conduit also has a generally rigid sleeve moveable between a cover position, wherein the sleeve covers a first part of the flexible section, and an uncovered position, wherein the sleeve does not cover the first part of a flexible section, to enable clamping of the conduit. The sleeve ensures that the conduit remains protected from inadvertent closure.

Other features and advantages of the present device will become apparent from the following detailed description, with reference to the accompanying drawings and claims, which form a part of the specification.

BRIEF DESCRIPTION OF THE DRAWINGS

In the accompanying drawings, which are incorporated in and constitute a part of this specification, numerous embodiments of the device described are illustrated, and together with the general description above, and the description below, exemplify the device of the present application.

DETAILED DESCRIPTION

Figure 1:
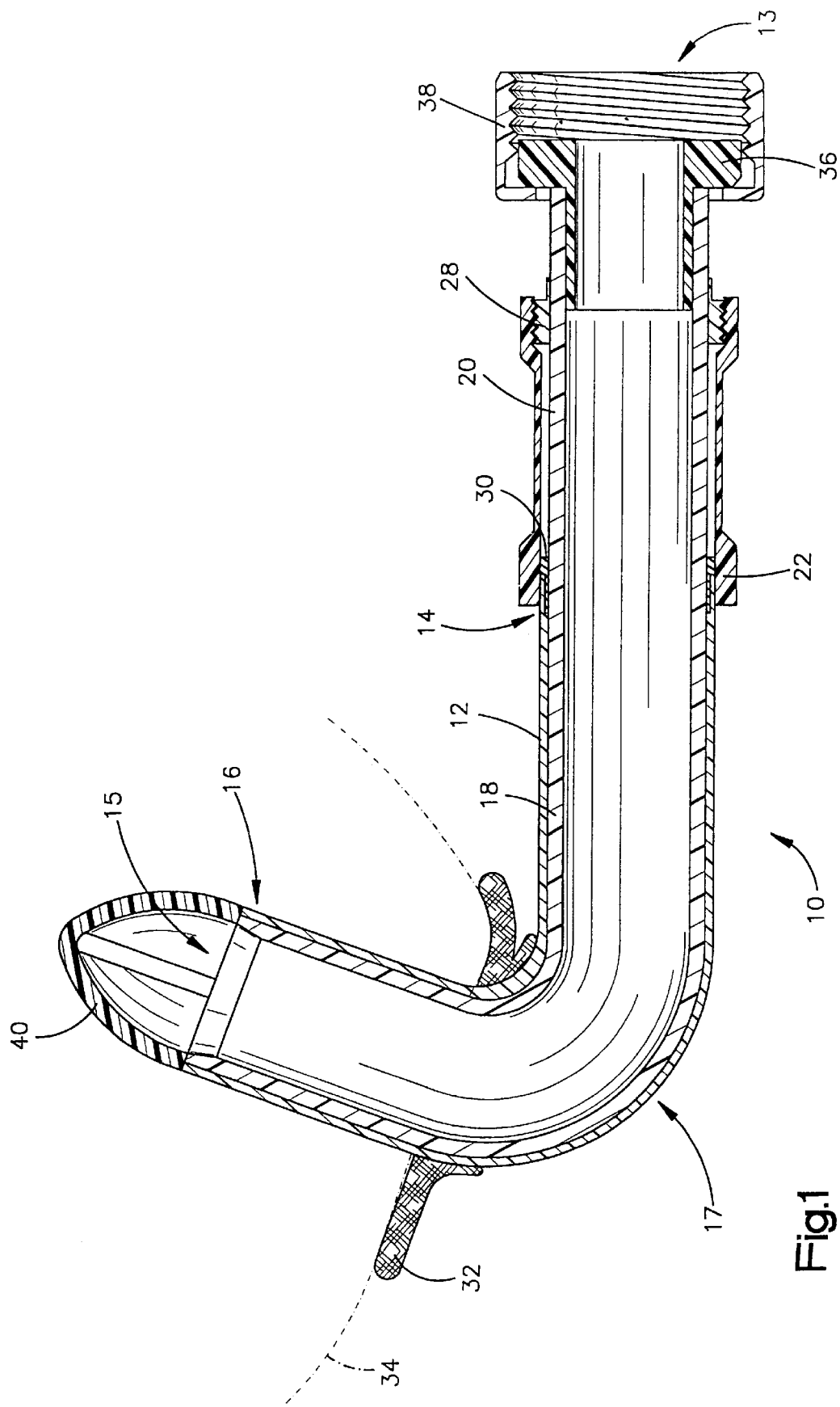
FIG. 1 is a side cross-sectional view of the cannula of the present invention shown with the sleeve in the cover position.

FIG. 1 shows the cannula of the present invention, generally designated 10. The cannula 10 has an inflow end 15 and an outflow end 13. The cannula 10 comprises a generally rigid layer 12 having a first end 14 and a second end 16. The cannula 10 further comprises a generally flexible tube 18 generally coaxial with the rigid layer 12. In the illustrated embodiment the flexible tube 18 extends from the first end 14 of the rigid layer to the second end 16 of the rigid layer 12, and has an axially extending portion 20 extending beyond the first end 14. However, it is not essential that the flexible tube 18 extend back to the first end 16, merely as long as the tube 16 includes an axially extending portion 20. The flexible tube 18 may be bonded to the rigid layer 12 with a biocompatible, or blood compatible, adhesive. A cuff 32 is mounted toward the second end 16 of the rigid layer 12. The cuff provides a surface for attaching the cannula 10 to the heart wall, shown in phantom as 34. In a preferred embodiment, the cuff 32 is a fabric, such as polyester fabric, and the cuff may be sewn to the heart wall 34.

The flexible tube is preferably a flexible polymer, such as polyurethane. The flexible tube 18 is also preferably coated with a biocompatible urethane, and/or blood compatible urethane, on its inner surface (i.e. its blood-contacting surface). The blood compatible coating may be located on top of the biocompatible coating. In an alternate embodiment, the rigid layer 12 is somewhat flexible to be molded and bent to a desired configuration. The form shown in FIGS. 1 and 2, which includes bend 17, shows merely one of many possible configuration of the cannula 10. The rigid layer 12 may be made of any suitable material, including titanium, titanium alloys, carbon fiber epoxy, and other materials. The rigid layer 12 is preferably made of a biocompatible material. Furthermore, the rigid layer 12 has a blood compatible coating on its blood contacting surfaces. The blood contacting surfaces of the rigid layer 12 are those portions within the heart wall 34; that is, forward of the cuff 32.

The cannula 10 further includes a generally rigid sleeve 22 that is coaxial with the rigid layer 12. The sleeve 22 is moveable between a cover position, as shown in FIG. 1, to an uncovered position shown in FIG. 2. The sleeve 22 is retained in the cover position by a fixation ring 28 having an external set of threads thereon. The sleeve 22 is preferably made from a titanium alloy, as is the fixation ring 28. The sleeve 22 has a set of cooperating threads which engage the fixation ring 28 to retain the sleeve 22 in the covered position. Nearly any manner of retaining means for retaining the sleeve 22 in the cover position may be used without departing from the scope of the present invention. A finishing ring 30 may be located adjacent the first end 14 of the rigid layer 12 to provide a finished edge to the outside of the cannula 10.

Outlet fitting 36 is disposed in the axially extending end 20 to receive a threaded tube (not shown) which delivers the blood to the ventricle assist device (not shown). The outlet fitting 36 (which is an inlet fitting in relation to the ventricle assist device) is preferably made of a titanium alloy. Clamp ring 38 retains the outlet fitting 36 in place, and is threaded to receive a corresponding threaded tube. The fixation ring 28 also clamps down on the outlet fitting 36 to provide a tight seal therebetween. A wire cage 40 is provided at the inflow end 15 of the cannula 10 to ensure the inflow end 15 remains in an open position.

Figure 2:
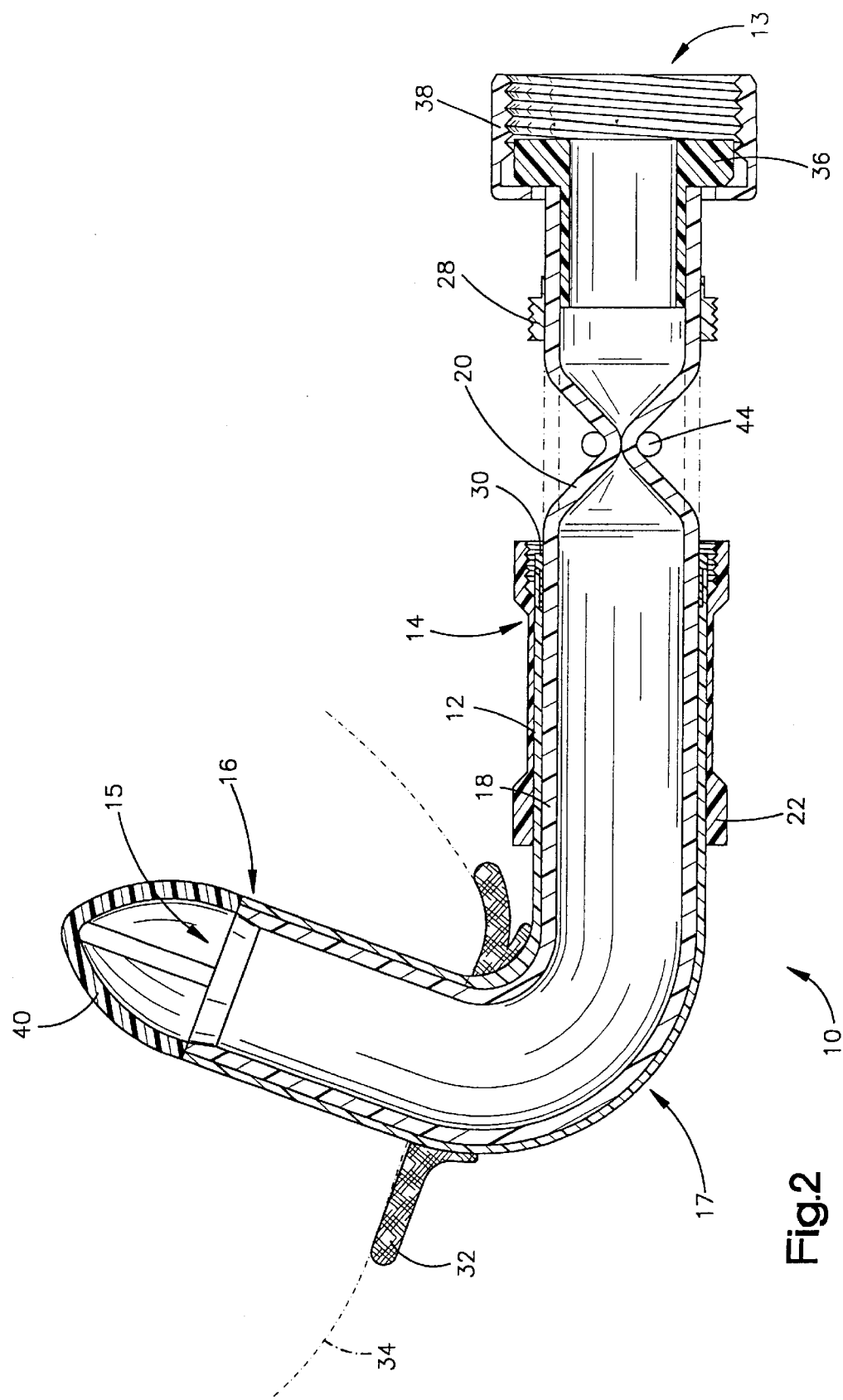
FIG. 2 is a side cross-sectional view of the cannula of FIG. 1, shown with the sleeve in the uncover position and being clamped with a clamp, with the unclamped shape of the cannula shown in hidden lines.

The clamping of the cannula 10 is as follows. As shown on FIG. 1, the sleeve 22 is in the cover position and covers the axially extending end 20 of the flexible tube 18. In this manner the cannula 10 is protected by the rigid layer 12 and the sleeve 22. Thus the cannula 10 avoids inadvertent closure due to pressure applied by internal organs, and also avoid kinking. When it is desired to clamp the cannula, the sleeve 22 is uncoupled from the fixation ring 28, and slid axially along the rigid layer 12 to the uncover position, as shown in FIG. 2. This leaves the axially extending end 20 of the flexible tube 18 exposed. A clamp 44, as shown in FIG. 2, may then be placed over the axially extending end 20 to block fluid flow through the cannula 10. When it is desired to allow flow to resume through the cannula 10, the clamp 44 is removed, and the tube 18 returns to its original form as shown in FIG. 1. The tube may return to its original shape by either the natural tendency of the tube, or the pressure of the blood in the cannula. The sleeve 22 may then be returned to the cover position and attached to the fixation ring 28. Various means may be used for moving the sleeve between the covered and uncovered position. For example, the sleeve 22 may be a split sleeve, thereby allowing it to be completely removed from the cannula 10.

It is to be further understood that several variations may be made without departing from the scope of the invention. For example, the sleeve 22 need not cover the entire axially extending end 20 of the flexible tube, but preferably covers substantially all of the end 20 when in the closed position to provide protection to the end 20 from kinking or closure. Furthermore, when in the uncovered position, the sleeve 22 may still cover a portion of the axially extending end 20. It is only required that enough of the axially extending end 20 be uncovered so as to allow the clamp 44 to be placed thereon. Furthermore, in an alternate embodiment the flexible tube 18 does not extend to the second end 16 of the rigid layer 12, and extends only to the first end 14.

Additionally, the radial orientation of the rigid layer 12 and the flexible tube 18 may be reversed such that the flexible tube 18 is radially outward of the rigid layer 12. However, care must be taken to ensure that the inner surface of the cannula 10 remains as blood compatible as possible. It is also within the scope of the present invention to have a cannula having a generally rigid section and a generally flexible section. In this case, the rigid section and flexible section are not necessarily different layers, but may different materials, or the same material having a different stiffness or rigidity. For example, the rigid section may be made from generally the same material as the flexible section, but the rigid section of the cannula may be treated so as to have increased stiffness, or may have chemicals added to it to make it stiffer. Alternately, the flexible section may instead be treated in order to make it more flexible, or both sections may be treated. In another embodiment, the flexible section may consist of a flexible material, and the rigid section may be made of the same material, but have a wire mesh, wire strands, or other stiffeners incorporated in the material to add stiffness to the rigid section.

As a further variation, the clampable portion of the cannula 10 may be located in the middle of the cannula. In this embodiment the cannula 10 may have a rigid layer 12 having a discontinuity or area of weakness formed therein, and the flexible tube 18 spans the discontinuity or area of weakness. The flexible tube 18 may or may not extend the entire length of the cannula. The rigid layer 12 may thus has a first portion and a second portion separated by the discontinuity. In this embodiment the sleeve 22 is moveable from a covered position, wherein it covers the exposed flexible tube 18, to an uncovered position, where the flexible tube 18 is exposed and enabled to be clamped.

Figure 3:
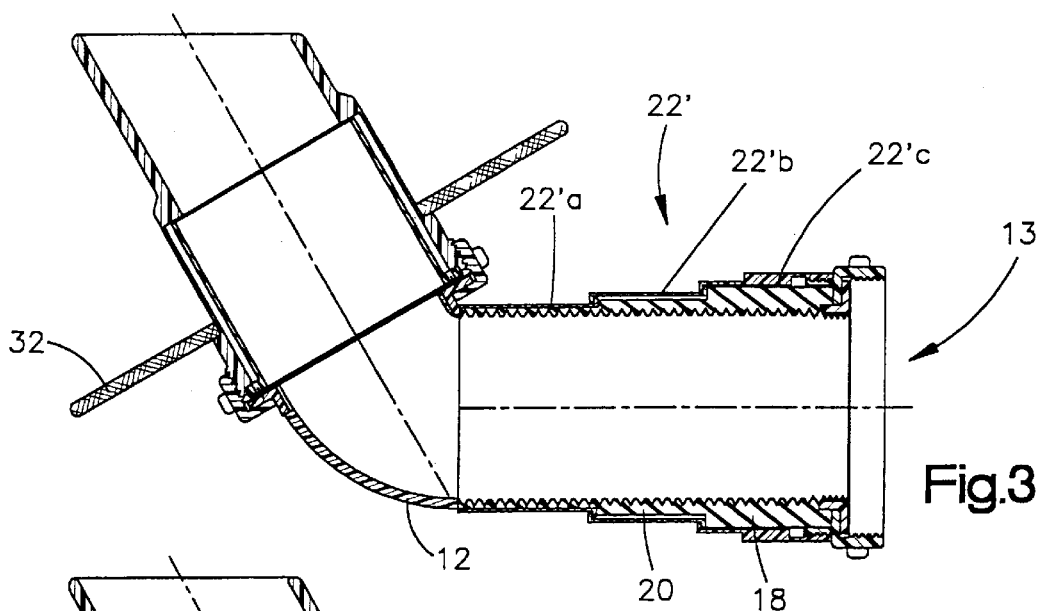
FIG. 3 is a side cross-sectional view of an alternate embodiment of the cannula of the present invention shown with the sleeve in the cover position.
Figure 4:
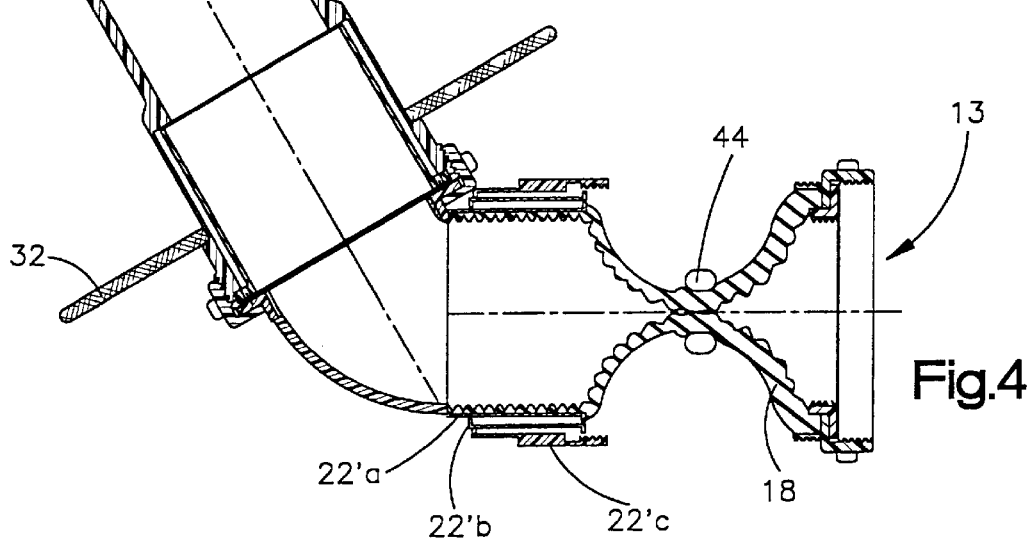
FIG. 4 is a side cross-sectional view of the cannula of FIG. 3, shown with the sleeve in the uncover position and being clamped with a clamp.
Figure 5:
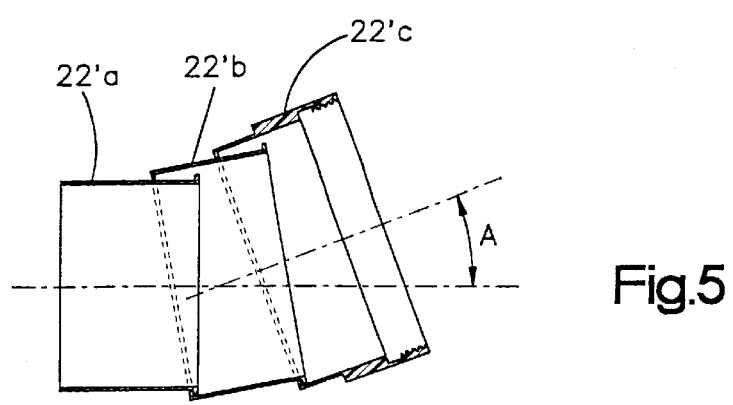
FIG. 5 is a side cross-sectional view of the sleeve shown in FIG. 3 with the sleeve bent at an angle.

An alternate embodiment of the sleeve 22 of the present invention is shown in FIGS. 3–5 as sleeve 22'. In this embodiment, the sleeve 22' has a telescopic shaped comprise of three portions 22'a, 22'b and 22'c. The telescopic shaped allows the sleeve to be used with cannulas that have limited axial lengths. The telescoping shape allows the sleeve to move axially such that the three portions 22'a, 22'b, and 22'c radially overlap to expose part of the flexible tube 18 for clamping (FIG. 4). Each telescopic portion preferably has an inner diameter sized to closely receive the flexible portion when in the closed position to eliminate gaps between the sleeve and the flexible tube 18. It is also desired to have relatively thick walls in the clampable portion of the cannula to increase the elasticity of the clampable portion. This is done to ensure that the clampable portion returns to its fully open shape when the clamp is removed, and also to ensure it remains in its fully open position when blood is flowing therethrough. In particular, it is desirable to avoid closure of the cannula due to pressure of adjacent internal organs, kinking, and closure due to differential pressure between the inside of the cannula and the surrounding environment. As shown in FIG. 5, the sleeve 22' has some flexibility to bend at an angle A to enable molding of the cannula in desired position. The flexible tube is shown in FIGS. 3 and 4 as including a plurality of grooves on its inner surface to increase the flexibility of the flexible tube 18.

The preferred form of the cannula has been described above. However, with the present disclosure in mind it is believed that obvious alterations to the preferred embodiments, to achieve comparable features and advantages, will become apparent to those of ordinary skill in the art.

What is claimed is:

1. An implantable conduit comprising:
   a generally rigid conduit having a first end;
   a generally flexible tube connected to said first end of said conduit; and
   a generally rigid sleeve which is slidable along said rigid conduit between a cover position wherein said sleeve covers a first part of said flexible tube and an uncovered position wherein said sleeve does not cover said first part of said flexible tube to enable clamping of said flexible tube.

2. The conduit of claim 1 wherein said sleeve is comprised of two or more portions which telescopically engage each other and cooperate such that the sleeve is movable between a cover position wherein said sleeve generally covers said flexible tube and an uncovered position where said sleeve generally does not cover said flexible tube.

3. The conduit of claim 2 wherein said flexible tube extends within said rigid conduit.

4. The conduit of claim 3 wherein said flexible tube extends substantially the entire length of said conduit.

5. The conduit of claim 1 wherein said flexible tube is coupled to said rigid conduit.

6. The conduit of claim 1 further comprising retainer means for securing said sleeve in said cover position.

7. The conduit of claim 6 wherein said retainer means includes cooperating threads on said sleeve and on said flexible tube.

8. The conduit of claim 7 wherein said retainer means further includes a threaded fixation ring coaxially mounted on said flexible tube, said fixation ring being located so as to receive said threads on said sleeve when said sleeve is in said cover position.

9. The conduit of claim 1 wherein said sleeve is made from a titanium alloy.

10. The conduit of claim 1 wherein said rigid conduit is moldable.

11. The conduit of claim 1 wherein said flexible tube is polyurethane.

12. The conduit of claim 11 wherein said flexible tube has a biocompatible surface.

13. The conduit of claim 11 wherein said flexible tube has a blood compatible inner surface.

14. The conduit of claim 1 wherein said rigid conduit is a titanium alloy.

15. The conduit of claim 1 further comprising a sealing ring on said first end of said rigid conduit.

16. The conduit of claim 1 wherein said conduit has an inlet and outlet and wherein said conduit further includes an outlet fitting on said outlet.

17. The conduit of claim 16 further comprising a wire cage coupled to said inlet.

18. The conduit of claim 1 further comprising a flexible cuff adjacent said rigid conduit for attaching said conduit to soft tissue.

19. The conduit of claim 18 wherein said rigid conduit has a bend.

20. The conduit of claim 1 wherein said rigid conduit has a blood compatible coating on its outer surface.

21. A clampable conduit comprising:

a generally rigid conduit having a first end;

a generally flexible tube in fluid communication with said first end of said conduit; and a generally rigid sleeve which is slidable along said rigid conduit between a cover position wherein said sleeve generally covers said flexible tube and an uncovered position wherein said sleeve generally does not cover said flexible tube.

22. A clampable conduit comprising:

a generally rigid tube having a first end;

a generally flexible tube section connected with said first end of said rigid tube such that said conduit may be clamped at said generally flexible tube section; and a generally rigid sleeve which is axially slidable along said rigid conduit between a cover position wherein said sleeve generally covers said flexible tube and an uncovered position wherein said sleeve generally does not cover said flexible tube.

23. The conduit of claim 22 further comprising means for retaining said sleeve in said cover position.

24. The conduit of claim 23 wherein said retaining means includes cooperating threads on said sleeve and on said rigid section.

25. The device of claim 22 wherein said conduit further comprises a sleeve comprised of two or more portions which telescopically engage each other and cooperate such that the sleeve is movable between a cover position which protects the flexible section and an uncovered position so that the flexible section may be clamped to shut off flow.

* * * * *

UNITED STATES PATENT AND TRADEMARK OFFICE
CERTIFICATE OF CORRECTION

PATENT NO. : 6,186,999 B1  
APPLICATION NO. : 09/141225  
DATED : February 13, 2001  
INVENTOR(S) : Ji-Feng Chen It is certified that error appears in the above-identified patent and that said Letters Patent is hereby corrected as shown below:

Col. 4, line 47, Claim 1, please insert -- the outside of -- after "along".

Col. 6, line 6, Claim 21, please insert -- the outside of -- after "along".

Col. 6, line 16, claim 22, please insert -- the outside of -- after "along".

Signed and Sealed this

Fifth Day of December, 2006

JON W. DUDAS  
*Director of the United States Patent and Trademark Office*